United States Patent [19]

Klaubert et al.

[11] 4,448,729
[45] May 15, 1984

[54] LEUCOTRIENE ANTAGONISTS

[75] Inventors: Dieter H. Klaubert, Perkiomenville; Anthony F. Kreft, III, Devon; Stanley C. Bell, Narberth, all of Pa.

[73] Assignee: American Home Products Corporation, New York, N.Y.

[21] Appl. No.: 411,200

[22] Filed: Aug. 25, 1982

[51] Int. Cl.³ .............. C07C 121/80; C07C 69/612; C07C 103/29
[52] U.S. Cl. .......................... 260/465 D; 260/465 E; 560/43; 562/452; 562/455; 564/167; 564/443; 424/304; 424/309; 424/319; 424/324; 424/330
[58] Field of Search .............. 564/443, 167; 260/465 D, 465 E; 560/43; 562/455, 452

[56] References Cited

U.S. PATENT DOCUMENTS

| 4,296,120 | 10/1981 | Kadin | 424/274 |
| 4,296,129 | 10/1981 | Kadin | 424/309 |
| 4,296,237 | 10/1981 | Cragoe | 544/405 |

FOREIGN PATENT DOCUMENTS 36663 9/1981 European Pat. Off. .

OTHER PUBLICATIONS

Appleton et al., J. Med. Chem., 20, 371–379 (1977).
Buckle et al., J. Med. Chem., 22, 158–168 (1979).
Samuelsson, TIPS Reviews, pp. 227–230, May 1980.
Marx, Science, 215, 1380–1383 (1982).

*Primary Examiner*—Dolph H. Torrence
*Attorney, Agent, or Firm*—Richard K. Jackson

[57] ABSTRACT

The compounds

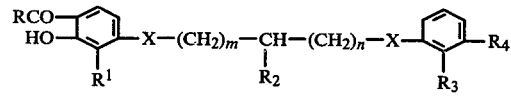

wherein each X is, independently, —O— or —NR$_5$, in which R$_5$ is hydrogen or alkyl; R is alkyl, R$_1$ is hydrogen or alkyl, R$_2$ is hydrogen, hydroxy, amino, alkylamino, dialkylamino or alkanoylamino and when m or n is 0, R$_2$ is hydroxymethyl, aminomethyl, alkylaminomethyl, dialkylaminomethyl or alkanoylaminomethyl; R$_3$ is hydrogen, —CN, —CONH$_2$ or —CO$_2$M in which M is hydrogen, alkyl or

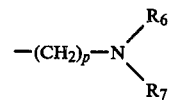

in which p is an integer from 2 to 6 and R$_6$ and R$_7$ are, independently, hydrogen or alkyl; R$_4$ is —NH$_2$, —NHCOR$_8$ in which R$_8$ is alkyl, —NHCOCO$_2$Z or —NHCOCH$_2$CH$_2$CO$_2$Z in which Z is hydrogen or alkyl; m and n are 0, 1, 2, 3 or 4 such that when n is from 1 to 4, m is 0 or 1 and when m is from 1 to 4, n is 0 or 1; or pharmaceutically acceptable salts thereof are leucotriene antagonists useful as antiallergy agents.

8 Claims, No Drawings

LEUCOTRIENE ANTAGONISTS

BACKGROUND OF THE INVENTION

The leucotrienes have been implicated as mediators of allergic and inflammatory responses associated with bronchial asthma and rheumatoid arthritis. The leucotrienes have been shown to dramatically constrict the pulmonary airways and small blood vessels. In the latter case, increased vascular permeability has been shown to occur after constriction by a leukotriene (Science 215 1380 (1982)).

The study of a series of chromone-2-carboxylic acid derivatives as antagonists of SRS-A (slow reacting substance of anaphylaxis, established by Samuelsson, Department of Chemistry, Karolinska Institutet, Stockholm, Sweden to be one or more leukotrienes—see TIPS, 227, May, 1980) led to the discovery of sodium 7-[3-(4-acetyl-3-hydroxy-2-propylphenoxy)-2-hydroxypropoxy]-4-oxo-8-propyl-4H-1-benzopyran-2-carboxylate (FPL 55712) which proved to be a specific antagonist of SRS-A and a standard for evaluating other inhibitors of SRS-A (J.Med.Chem. 20 371 (1977).

Buckle et al., J.Med.Chem. 22 158 (1979) reported on a number of aryloxyalkyloxy- and aralkyloxy-4-hydroxy-3-nitrocoumarins as antagonists of SRS-A and inhibitors of histamine release. European Pat. No. 0036663 discloses certain oxiranbutyric acid esters as antagonists of SRS-A. U.S. Pat. No. 4,296,237 discloses 3-hydroxy-4-substituted-3-pyrroline-2,5-diones as specific antagonists of SRS-A. U.S. Pat. No. 4,296,120 discloses (carboxy-oxo-pyrrolidino)phenyl alkenamides and esters as SRS-A antagonists. U.S. Pat. No. 4,296,129 discloses (carboxyacylamino)phenyl alkenamides and esters as SRS-A antagonists.

DESCRIPTION OF THE INVENTION

In accordance with this invention there is provided a group of antiallergy agents which function as inhibitors of leukotriene induced reaction of contractile animal tissue. The compounds of this invention are of the following structural formula:

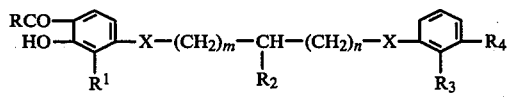

wherein
each X is, independently, —O— or —NR$_5$—, in which R$_5$ is hydrogen or alkyl of 1 to 6 carbon atoms;
R is alkyl of 1 to 6 carbon atoms;
R$_1$ is hydrogen or alkyl of 1 to 6 carbon atoms;
R$_2$ is hydrogen, hydroxy, amino, alkylamino of 1 to 6 carbon atoms, dialkylamino of 2 to 12 carbon atoms, or alkanoylamino of 2 to 6 carbon atoms; and when m or n is 0, R$_2$ is hydroxymethyl, aminomethyl, alkylaminomethyl of 2 to 7 carbon atoms, dialkylaminomethyl of 5 to 13 carbon atoms or alkanoylaminomethyl of 5 to 7 carbon atoms;
R$_3$ is hydrogen, —CN, —CONH$_2$ or —CO$_2$M in which M is hydrogen, alkyl of 1 to 6 carbon atoms or

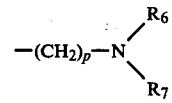

in which p is one of the integers from 2 to 6 and R$_6$ and R$_7$ are, independently, hydrogen or alkyl of 1 to 6 carbon atoms;
R$_4$ is —NH$_2$, —NHCOR$_8$ where R$_8$ is alkyl of 1 to 6 carbon atoms, —NHCOCO$_2$Z or —NHCOCH$_2$CH$_2$CO$_2$Z where Z is hydrogen or alkyl of 1 to 6 carbon atoms;
m and n are 0, 1, 2, 3 or 4 such that when n is from 1 to 4, m is 0 or 1 and when m is from 1 to 4, n is 0 or 1;
or a pharmaceutically acceptable salt thereof.

The pharmaceutically acceptable salts of the compounds of this invention include addition salts derived from organic or inorganic acids such as hydrochloric, hydrobromic, sulfuric, phosphoric, methane sulfonic, nitric, p-toluene sulfonic, acetic, citric, maleic, succinic acid and the like. In addition, the compounds in their free carboxylic acid form are converted by standard techniques well-known to the chemist into alkali metal (sodium or potassium), alkaline earth metal (calcium or magnesium), ammonium or primary, secondary and tertiary alkylamine salts, the latter containing from 1 to 6 carbon atoms in their alkyl moieties.

A preferred group of compounds of this invention from the standpoint of production economics are those of the formula:

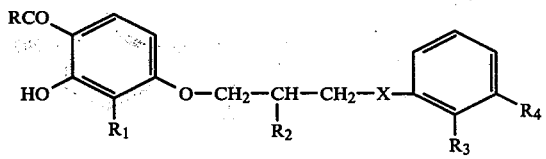

wherein
R is ethyl or methyl;
R$_1$ is hydrogen or alkyl of 1 to 6 carbon atoms;
R$_2$ is hydrogen or hydroxyl;
X is —O— or —NH—;
R$_3$ is hydrogen, —CN or —CONH$_2$; and
R$_4$ is —NH$_2$ or —NHCOCO$_2$Z where Z is hydrogen or alkyl of 1 to 6 carbon atoms;
or a pharmaceutically acceptable salt thereof.

In addition, the intermediates, where R$_4$ in the structural formulae, supra, is a nitro group, represent another aspect of the invention. Although some of the nitro substituted compounds demonstrate a degree of inhibition of leucotriene activity, their activity level is generally not that of the corresponding amines and substituted amines.

For example, the nitro substituted intermediate for the product of Example 7, is actually a potentiator of the anaphylactic tissue response, while the nitro substituted intermediate of Example 10 exhibited 62 percent inhibition at 10$^{-4}$M concentration (EC$_{50}$=7.6×10$^{-5}$M) in the Schultz-Dale reaction employing sensitized guinea pig trachea.

The compounds of this invention, are readily prepared by reaction of an appropriately substituted phenol of the formula:

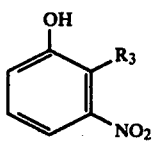

with an epoxide of the formula:

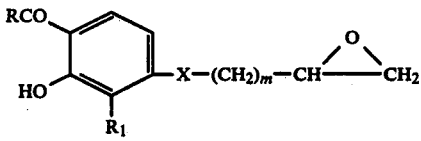

to yield predominately the beta hydroxy ether—

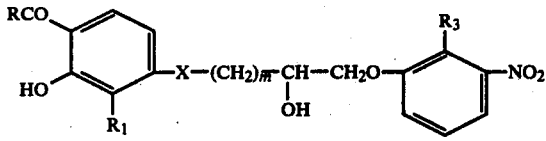

—with smaller amounts of the isomeric methylol product—

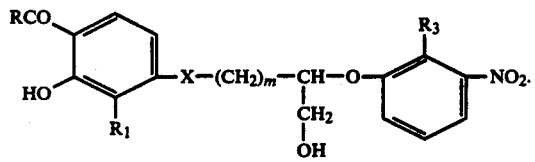

In an analogous manner,

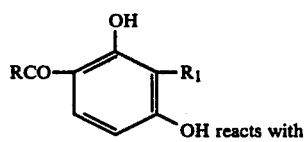

OH reacts with

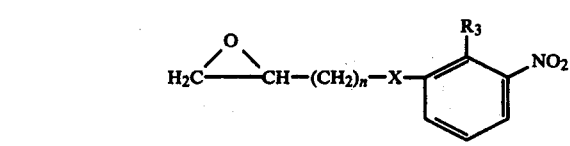

to yield predominately—

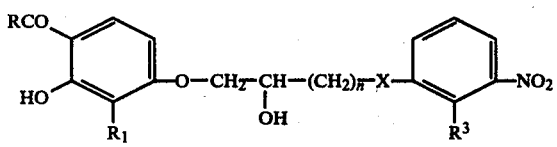

—and its isomeric methylol analogues—

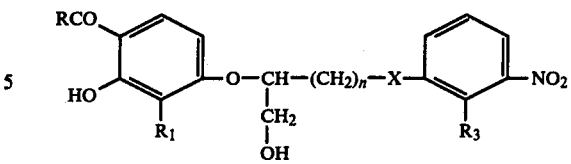

The nitro group is then reduced to the amino substituent.

The compounds in which both X groups are nitrogen are similarly produced by reaction of the epoxide reactant with an appropriately substituted amine rather than a phenol. Thus, in the reactions depicted supra, substitution of

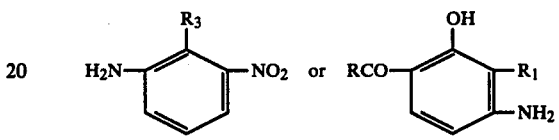

for the respective phenols (with protection of the hydroxyl group) yields the desired products.

Each of the variables $R-R_3$, X, m and n are defined supra. $R_4$ is maintained as a nitro group during reaction with the epoxide and is then reduced to the amino group. Acylation of the $R_4$ amino group is performed routinely with the acid halides of the desired $R_8CO-$, $ZO_2CCO-$ and $ZO_2CCH_2CH_2CO-$ acyl groups.

The aliphatic hydroxy substituent is readily converted to a primary, secondary or tertiary amine by conversion to a halogen with $PCl_3$, $PCl_5$, $POCl_3$, $SOCl_2$ or analogous halogenating agents followed by routine amination with ammonia or a primary or secondary amine. The alkanoylamine is produced by acylation with the desired alkanoyl halide or other conventional acylating reagents.

The following examples illustrate the production of representative compounds of the invention.

EXAMPLE 1

2-[3-(4-Acetyl-3-hydroxy-2-propylphenoxy)-2-hydroxypropoxy]-6-aminobenzonitrile To a solution of 34 g of 2-hydroxy-6-nitrobenzonitrile and 60 g of 4'-(2,3-epoxy)propoxy-2'-hydroxy-3'-propylacetophenone in 450 ml of dry DMF is added 30 drops Triton ® B. The solution is refluxed under nitrogen for 1.5 hr. The solvent is then evaporated and the residue is taken up in 500 ml ethyl acetate, washed sequentially with 500 ml 0.5N sodium hydroxide, then 500 ml water. After drying over magnesium sulfate the organic layer is evaporated to 83 g of crude product. Chromatography on silica gel eluting with 95/5 methylene chloride/ethyl acetate gives 31.4 g (34%) of 2-[3-(4-acetyl-3-hydroxy-2-propylphenoxy)-2-hydroxypropoxy]-6-nitrobenzonitrile as a white crystalline solid, m.p. 117°–119° C.

Analysis for: $C_{21}H_{22}N_2O_7$; Calculated: C, 60.86; H, 5.35; N, 6.67; Found: C, 60.63; H, 5.48; N, 6.74.

A solution of 10 g of 2-[3-(4-acetyl-3-hydroxy-2-propylphenoxy)-2-hydroxypropoxy]-6-nitrobenzonitrile, 2.5 g 10% Pd on carbon and 10 g cyclohexene in 500 ml absolute ethanol is refluxed for 30 min. The reaction mixture is cooled to room temperature, filtered through Celite and freed of solvent. Trituration with diethyl ether and drying of the insolubles gives 6.1 g of the title compound as a white solid, m.p. 123°–125° C.

Analysis for: $C_{21}H_{24}N_2O_5$; Calculated: C, 65.61; H, 6.29; N, 7.29; Found: C, 65.69; H, 6.29; N, 7.42.

EXAMPLE 2

[[3-[3-(4-Acetyl-3-hydroxy-2-propylphenoxy)-2-hydroxypropoxy]-2-cyanophenyl]amino]oxoacetic acid ethyl ester To A solution of 1.0 g 2-[3-(4-acetyl-3-hydroxy-2-propylphenoxy)-2-hydroxypropoxy]-6-aminobenzonitrile in 20 ml methylene chloride at 0° C. under nitrogen is added 0.27 ml ethyl oxalyl chloride. After 40 min at 0° C. the reaction mixture is allowed to warm to room temperature and stirring is continued for 3 hr. The reaction mixture is then added to saturated sodium bicarbonate solution. The organic layer is separated and dried over magnesium sulfate. The solvent is removed in vacuo and the residue is triturated with 25 ml hot ethanol. The ethanol-insoluble solid is dried in vacuo to afford 0.67 g of the title compound as a white solid (62%), m.p. 172°–174° C.

Analysis for: $C_{25}H_{28}N_2O_8 \cdot \frac{1}{2}EtOH$; Calculated: C, 61.53; H, 6.16; N, 5.52; Found: C, 61.25; H, 5.85; N, 5.62.

EXAMPLE 3

[[3-[-(4-Acetyl-3-hydroxy-2-propylphenoxy)-2-hydroxypropoxy]-2-cyanophenyl]amino]oxoacetic acid sodium salt A suspension of 1.54 g [3-[3-(4-acetyl-3-hydroxy-2-propylphenoxy)-2-hydroxypropoxy]-2-cyanophenyl]amino]oxoacetic acid ethyl ester and 0.240 mg sodium bicarbonate in a mixture of 30 ml of 5:1 methanol/water is refluxed for 2 hr. The solvent is evaporated and the residue is taken up in 50 ml hot acetonitrile. Cooling the solution to room temperature affords 0.9 g of the title compound as a white solid.

Analysis for: $C_{23}H_{23}N_2O_8Na \cdot \frac{1}{2}H_2O$; Calculated: C, 56.67; H, 4.96; N, 5.75; Found: C, 56.74; H, 4.82; N, 5.91.

EXAMPLE 4

1-[2-Hydroxy-3-propyl-4-[2-hydroxy-3-(3-aminophenoxy)propoxy]phenyl]ethanone

The desired compound is prepared in two steps by the method of Example 1 but using 3-nitrophenol and 4'-(2,3-epoxy)-propoxy-2'-hydroxy-3'-propylacetophenone. A white solid is obtained m.p. 85°–89° C.

Analysis for: $C_{20}H_{25}NO_5$; Calculated: C, 66.83; H, 7.01; N, 3.90; Found: C, 66.78; H, 6.96; N, 3.80.

EXAMPLE 5

[[3-[3-(4-Acetyl-3-hydroxy-2-propylphenoxy)-2-hydroxypropoxy]phenyl]amino]oxoacetic acid ethyl ester The desired compound is prepared by the method of Example 2 but using 1-[2-hydroxy-3-propyl-4-[2-hydroxy-3-(3-aminophenoxy)propoxy]phenyl]ethanone. A white solid is obtained, m.p. 98°–101° C.

Analysis for: $C_{24}H_{29}NO_8$; Calculated: C, 62.73; H, 6.36; N, 3.05; Found: C, 62.50; H, 6.25; N, 2.97.

EXAMPLE 6

2-Amino-6-[[3-(4-acetyl-3-hydroxy-2-propylphenoxy)-2-hydroxypropyl]amino]benzonitrile The desired compound is prepared by the method of Example 1 but using 2-[[3-(4-acetyl-3-hydroxy-2-propylphenoxy)-2-hydroxypropyl]amino]-6-nitrobenzonitrile. A white solid is obtained, m.p. 111°–114° C.

Analysis for: $C_{21}H_{25}N_3O_4$; Calculated: C, 65.78; H, 6.57; N, 10.96; Found: C, 65.36; H, 6.63; N, 10.71.

EXAMPLE 7

[[[3-[3-(4-acetyl-3-hydroxy-2-propylphenoxy)-2-hydroxypropyl]amino]-2-cyanophenyl]amino]oxoacetic acid ethyl ester The desired product is prepared by the method of Example 2 but using 2-amino-6[[3-(4-acetyl-3-hydroxy-2-propylphenoxy)-2-hydroxypropyl]amino]benzonitrile. A white solid is obtained, m.p. 166°–169° C.

Analysis for: $C_{25}H_{29}N_3O_7$; Calculated: C, 62.10; H, 6.05; N, 8.69; Found: C, 61.92; H, 6.08; N, 8.47.

EXAMPLE 8

[[[3-[3-(4-Acetyl-3-hydroxy-2-propylphenoxy)-2-hydroxypropyl]amino]-2-cyanophenyl]amino]oxoacetic acid sodium salt The desired product is prepared by the method of Example 3 but using [[[3-[3-(4-acetyl-3-hydroxy-2-propylphenoxy)-2-hydroxypropyl]amino]-2-cyanophenyl]amino]oxoacetic acid ethyl ester. A white solid is obtained, m.p. 134°–140° C. (decomp.)

Analysis for: $C_{23}H_{24}N_3O_7Na \cdot \frac{1}{2}H_2O$; Calculated: C, 57.31; H, 5.12; N, 8.80; Found: C, 57.03; H, 5.01; N, 8.78.

EXAMPLE 9

2-[3-(4-Acetyl-3-hydroxy-2-propylphenoxy)-2-hydroxypropyl]amino-6-aminobenzamide This compound is formed as a minor product in the synthesis of 2-amino-6-[[3-(4-acetyl-3-hydroxy-2-propylphenoxy)-2-hydroxypropyl]amino]benzonitrile as in Example 9. A white solid is obtained, m.p. 151°–154° C.

Analysis for: $C_{21}H_{21}N_3O_5$; Calculated: C, 62.82; H, 6.78; N, 10.47; Found: C, 62.47; H, 6.64; N, 10.18.

EXAMPLE 10

1-[2-Hydroxy-4-[2-hydroxy-3-(3-nitrophenoxy)propoxy]phenyl]ethanone

The desired compound is prepared by the method of Example 1 but using 3-nitrophenol and 4'-(2,3-epoxy)-propoxy-2'-hydroxy-acetophenone. A yellow solid is obtained, m.p. 119°–122° C.

Analysis for: $C_{17}H_{17}NO_7$; Calculated: C, 58.78; H, 4.93; N, 4.03; Found: C, 58.51; H, 5.06; N, 3.95.

The antiallergy activity of the compounds of this invention was established by the Schultz-Dale reaction employing sensitized guinea pig trachea by the following procedure:

Guinea pigs weighing from about 275 to 325 g. are sensitized to ovalbumin. Three to four weeks later, tracheae are removed under $CO_2$ anesthesia. Excess tissue is removed and each trachea is spirally cut and suspended under 6 g. tension in a tissue bath (37° C.) containing modified Tyrode's solution (pH 7.4) oxygenated with a 95 percent $O_2$–5 percent $CO_2$ gas mixture. The Tyrodes composition (mmol) is: NaCl, 139.2; KCl, 2.7; $MgSO_4 \cdot 7H_2O$, 0.49; $NaHCO_3$, 11.9; $NaH_2PO_4 \cdot H_2O$, 0.4; $CaCl_2 \cdot 2H_2O$, 1.8 and glucose, 5.5. Tracheae are allowed to equilibrate for 90 minutes before exposure to agonists or drugs.

A response to histamine is elicited at two bath concentrations ($1 \times 10^{-6}M$ and $1 \times 10^{-4}M$). The lower concentration primes the tissue and is allowed a 5 minute contact period. The higher concentration (10 minute exposure) produces a maximal response for the tissue. In each case, the bath fluid is replaced and the tissue is washed two times with fresh Tyrode solution. Compounds tested are introduced into the bath to produce a $10^{-4}$M concentration twenty minutes after the second histamine treatment (subsequent testing at $10^{-5}$ and $10^{-6}$M bath concentrations are employed in dose-response analyses). Ovalbumin (8 μg/ml) is introduced into the bath ten minutes later.

Tracheal contractions following histamine, drug and antigen treatment are continuously monitored with a Statham force displacement transducer and the measurement of grams tension is graphically displayed on a Beckman Dynograph recorder and digitally recorded on a Texas Instruments printer.

The contracture curve following antigen challenge is compared with the maximal histamine response at 10 minute time intervals up to 90 minutes and the responses are expressed as percentage inhibition. The area under the curve is calculated for each time period. Mean value of the area under the curve (each from no less than three tissues) for each time period are compared with comparable area under the curve calculations from control (no drug) tissues to obtain the percentage inhibition. The $EC_{50}$ is calculated from the area under the curve values at 90 minutes to define the effective concentration of test compound which produces a 50 percent reduction in area under the curve compared to control tissues.

Following the same basic procedure, guinea pig lung parenchyma strips (25×3×3 mm) dissected along the distal edges of two different lobes are suspended under 1 g. tension in the tissue bath. Equilibration in the Tyrode solution is conducted for 45 minutes with complete solution changes at 15 minute intervals. Maximal contraction induced with histamine (50 μM) primes the tissue. Five minutes later, the bath fluid is exchanged two times and the tissues are allowed to equilibrate 15 minutes longer. The test compound is then introduced into the bath to give a $10^{-4}$M solution. Five minutes later the ovalbumin challenge (8 μg/ml) is given. The data is collected at ten minute intervals up to 60 minutes and analysed as with the guinea pig trachea technique.

SCHULTZ-DALE STUDIES OF GUINEA PIG ISOLATED RESPIRATORY TISSUE

| Example | Test Concentration (M) | Tracheal Spirals % Inhibition at 90 minutes | $EC_{50}$ (M) | Parenchymal Strips % Inhibition at 60 minutes |
|---|---|---|---|---|
| 1 | $10^{-4}$ | 64.15* | | |
|   | $10^{-5}$ | 45.66* | $2.0 \times 10^{-5}$ | |
|   | $10^{-6}$ | 20.56 | | |
| 2 | $10^{-4}$ | 72.96* | | 65.50* |
|   | $10^{-5}$ | 62.96* | $8.7 \times 10^{-6}$ | 2.09 |
|   | $10^{-6}$ | 18.76 | | |
| 3 | $10^{-4}$ | 62.13* | | 22.91 |
|   | $10^{-5}$ | 21.53 | $5.3 \times 10^{-5}$ | |
|   | $10^{-6}$ | 12.77 | | |
| 4 | $10^{-4}$ | 76.25* | | |
|   | $10^{-5}$ | 9.07 | $3.6 \times 10^{-5}$ | |
|   | $10^{-6}$ | 4.98 | | |
| 5 | $10^{-4}$ | 52.97* | | |
|   | $10^{-5}$ | 22.77 | $9.7 \times 10^{-5}$ | |
|   | $10^{-6}$ | 8.57 | | |
| 6 | $10^{-4}$ | 38.82* | | |
| 7 | $10^{-4}$ | 63.77* | | |
|   | $10^{-5}$ | 39.34 | $3.0 \times 10^{-5}$ | |
|   | $10^{-6}$ | 2.64 | | |
| 8 | $10^{-4}$ | 63.47* | | |
|   | $10^{-5}$ | 37.49* | $2.5 \times 10^{-5}$ | |
|   | $10^{-6}$ | 28.36 | | |

SCHULTZ-DALE STUDIES OF GUINEA PIG ISOLATED RESPIRATORY TISSUE -continued

| Example | Test Concentration (M) | Tracheal Spirals % Inhibition at 90 minutes | $EC_{50}$ (M) | Parenchymal Strips % Inhibition at 60 minutes |
|---|---|---|---|---|
| 9 | $10^{-4}$ | 40.72* | | |

*Significant difference from control at 0.05 level w/ Dunnett's "t" test.

In addition, the product of Example 2, as a representative antiallergy agent of this invention, was established as an inhibitor of leucotriene D$_4$ in the Schultz-Dale reaction employing guinea pig ileal tissue at a $pA_2 = 9.4$ level (see Ott et al., J.Pharm.Meth. 5 75–92 (1981)).

The antiallergy agents of this invention are useful in the treatment and prevention of leucotriene induced anaphylaxis. In particular, the compounds of this invention are useful in treating and preventing bronchial asthma, allergic rhinitis and skin disorders in humans and animals. As such, the compounds are administered to the patient either orally or parenterally, alone or in combination with a pharmaceutically acceptable carrier or vehicle in accordance with standard pharmaceutical procedures. The dosage of the antiallergy agents of this invention must be personalized for the patient and will vary according to the age, weight, desired response and severity of the patients' symptoms. Similarly, the dosage regimen will vary with the selected route of administration.

What is claimed is:

1. A compound of the formula

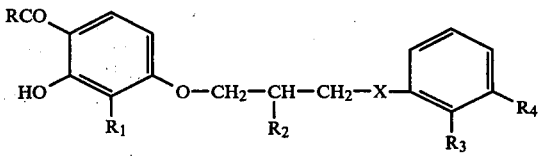

wherein
R is ethyl or methyl
R$_1$ is hydrogen or alkyl of 1 to 6 carbon atoms;
R$_2$ is hydrogen or hydroxyl;
X is —O— or —NH—;
R$_3$ is hydrogen, —CN or —CONH$_2$; and
R$_4$ is —NH$_2$ or —NHCOCO$_2$Z where Z is hydrogen or alkyl of 1 to 6 carbon atoms;
or a pharmaceutically acceptable salt thereof.

2. The compound of claim 1 which is 2-[3-(4-Acetyl-3-hydroxy-2-propylphenoxy)-2-hydroxypropoxy]-6-aminobenzonitrile or a pharmaceutically acceptable salt thereof.

3. The compound of claim 1 which is [[3-[3-(4-Acetyl-3-hydroxy-2-propylphenoxy)-2-hydroxypropoxy]-2-cyanophenyl]amino]oxoacetic acid ethyl ester or a pharmaceutically acceptable salt thereof.

4. The compound of claim 1 which is 1-[2-hydroxy-3-propyl-4-[2-hydroxy-3-(3-aminophenoxy)propoxy]-phenyl]ethanone or a pharmaceutically acceptable salt thereof.

5. The compound of claim 1 which is [[3-[3-(4-acetyl-3-hydroxy-2-propylphenoxy)-2-hydroxypropoxy]-phenyl]amino]oxoacetic acid ethyl ester or a pharmaceutically acceptable salt thereof.

6. The compound of claim 1 which is 2-amino-6-[[3-(4-acetyl-3-hydroxy-2-propylphenoxy)-2-hydroxypropyl]amino]benzonitrile or a pharmaceutically acceptable salt thereof.

7. The compound of claim 1 which is [[[3-[3-(4-acetyl-3-hydroxy-2-propylphenoxy)-2-hydroxypropyl]amino]-2-cyanophenyl]amino]oxoacetic acid ethyl ester.

8. The compound of claim 1 which is 2-[3-(4-acetyl-3-hydroxy-2-propylphenoxy)-2-hydroxypropyl]-amino-6-aminobenzamide or a pharmaceutically acceptable salt thereof.

* * * * *